United States Patent
Raney et al.

(10) Patent No.: US 9,572,711 B2
(45) Date of Patent: Feb. 21, 2017

(54) MULTIPLE FREQUENCY PHACOEMULSIFICATION NEEDLE DRIVER

(71) Applicant: Abbott Medical Optics Inc., Santa Ana, CA (US)

(72) Inventors: Rob Raney, Laguna Beach, CA (US); David A. King, Pleasanton, CA (US); David A. Greenbaum, Costa Mesa, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 589 days.

(21) Appl. No.: 14/018,144

(22) Filed: Sep. 4, 2013

(65) Prior Publication Data

US 2014/0005707 A1    Jan. 2, 2014

Related U.S. Application Data

(62) Division of application No. 12/613,570, filed on Nov. 6, 2009, now Pat. No. 8,545,528.

(Continued)

(51) Int. Cl.
*A61F 9/007* (2006.01)
*A61B 17/32* (2006.01)
(Continued)

(52) U.S. Cl.
CPC .... *A61F 9/00745* (2013.01); *A61B 17/320068* (2013.01); *A61B 18/1206* (2013.01);
(Continued)

(58) Field of Classification Search
CPC ............... A61F 9/00745; Y10T 307/50; A61B 18/1206; A61B 17/320068; A61B 2017/00146; A61B 2017/0015; A61B 2018/1273

See application file for complete search history.

(56) References Cited

U.S. PATENT DOCUMENTS 2,763,840 A    9/1956 Pfleger
3,469,213 A    9/1969 Leonard
(Continued)

FOREIGN PATENT DOCUMENTS

EP    1625836 A1    2/2006
EP    1849444 A1    10/2007
WO    WO-0152782 A1    7/2001

OTHER PUBLICATIONS

International Search Report and Written Opinion, mailed May 3, 2010, and International Preliminary Report on Patentability, mailed May 10, 2011, for Application No. PCT/US2009/063484, 16 pages.

*Primary Examiner* — Julian W Woo
(74) *Attorney, Agent, or Firm* — Abbott Medical Optics Inc.

(57) ABSTRACT

A system for performing an ocular surgical procedure is provided. The system includes a multiple frequency signal source, a configurable tuned output filter connected to the multiple frequency signal source, and a multiple frequency ultrasonic handpiece. The multiple frequency signal source operates at a first frequency and is configured to drive the configurable filter and the multiple frequency ultrasonic handpiece at the first frequency. The multiple frequency signal source operates at a second frequency and is configured to drive the configurable filter and the multiple frequency ultrasonic handpiece at the second frequency, and the design addresses third harmonic frequency issues for the multiple frequency ultrasonic handpiece. Switchable passive components, such as inductors, resistors, and/or capacitors may be employed in the configurable tuned output circuit, or (Continued)

alternately multiple similar circuits may be employed. Alternately, a multi-tap transformer may be provided.

7 Claims, 10 Drawing Sheets

Related U.S. Application Data

(60) Provisional application No. 61/112,626, filed on Nov. 7, 2008.

(51) Int. Cl.
*A61B 18/12* (2006.01)
*A61B 17/00* (2006.01)

(52) U.S. Cl.
CPC ............ *A61B 2017/0015* (2013.01); *A61B 2017/00146* (2013.01); *A61B 2018/1273* (2013.01); *Y10T 307/50* (2015.04)

(56) References Cited

U.S. PATENT DOCUMENTS

| | | | |
|---|---|---|---|
| 4,012,647 A | | 3/1977 | Balamuth et al. |
| 4,063,557 A | | 12/1977 | Wuchinich et al. |
| 4,156,187 A | * | 5/1979 | Murry ............ A61B 17/22012 324/142 |
| 4,378,538 A | | 3/1983 | Gignoux |
| 5,019,794 A | | 5/1991 | Letessier et al. |
| 5,162,759 A | | 11/1992 | Yajima |
| 5,406,503 A | | 4/1995 | Williams, Jr. et al. |
| 5,451,161 A | | 9/1995 | Sharp |
| 5,897,569 A | * | 4/1999 | Kellogg ........... A61B 17/32006 310/316.01 |
| 6,588,277 B2 | * | 7/2003 | Giordano ......... A61B 17/32006 606/169 |
| 6,945,981 B2 | * | 9/2005 | Donofrio ......... A61B 17/32006 604/22 |
| 6,997,935 B2 | * | 2/2006 | Anderson ........... A61F 9/00745 323/212 |
| 7,671,693 B2 | | 3/2010 | Brobston et al. |
| 2002/0010477 A1 | | 1/2002 | Hirt et al. |
| 2008/0139994 A1 | | 6/2008 | Mackool et al. |

\* cited by examiner

MULTIPLE FREQUENCY PHACOEMULSIFICATION NEEDLE DRIVER

This application is a divisional application and claims priority to U.S. application Ser. No. 12/613,570, entitled "Multiple Frequency Phacoemulsification Needle Driver", filed on Nov. 6, 2009, which is a non-provisional of U.S. application No. 61/112,626, filed on Nov. 7, 2008, the entire contents of each are hereby incorporated by reference in their entirety for all purposes as if fully set forth herein.

BACKGROUND OF THE INVENTION

Field of the Invention

The present invention relates generally to the field of ocular surgery, and more specifically to a method and apparatus for controlling a phacoemulsification handpiece and needle configured for operation at multiple ultrasonic frequencies during ophthalmic surgical procedures.

Description of the Related Art

Phacoemulsification surgery has been successfully employed in the treatment of certain ocular problems, such as cataract surgery, including removal of a cataract-damaged lens and implantation of an intraocular lens. Phacoemulsification surgery typically involves removal of the cataract-damaged lens and may utilize a small incision at the edge of the cornea. Through the small incision, the surgeon then creates an opening in the capsule, i.e. membrane that encapsulates the lens.

The surgeon can insert an ultrasonic probe, incorporated within a phacoemulsification handpiece, through the opening in the cornea and capsule accessing the damaged lens. The handpiece's ultrasonically actuated tip emulsifies the damaged lens sufficient to be evacuated by the handpiece. After the damaged natural lens is completely removed, the handpiece tip is withdrawn from the eye. The surgeon may now implant an intraocular lens into the space made available in the capsule.

While performing phacoemulsification surgical techniques, such as lens removal, the surgeon may desire to employ either a longitudinal motion or a mix of longitudinal with transversal motions, also referred to in the industry as transverse phacoemulsification, to affect different desired cutting movements. Certain previously available ultrasonic probe designs provided for only one type of cutting movement such that if the surgeon determines during the procedure a need to switch from, for example, longitudinal to transverse cutting movements, the surgeon has been required to change the ultrasonic probe handpiece. This changing of the handpiece during surgery can complicate and lengthen the procedure.

It is desirable to provide the surgeon with a single handpiece capable of operating in either the longitudinal or transverse modes or some mix of them that provides an elliptical mode. The frequency of handpiece operation for longitudinal or transverse modes are determined by the physical and electrical properties of an ultransonic handpiece. The operational frequencies are on or about the resonant frequencies of the handpiece and these frequencies are generally different for longitudinal and transverse modes. The driver of such a handpiece must therefore operate at multiple frequencies.

Past handpiece drivers were linear class AB types or similar. Although these drivers exhibited a flat (acceptable) frequency response and were therefore capable of handling a multiple frequency handpiece, they were very inefficient in power delivery, required heatsinking, had a high quiescent current, suffered from crossover distortion, and were generally complex designs. Power dissipation in these drivers is high and the resulting heat can be destructive if not properly managed.

Modern handpiece drivers are class D designs. A class D driver is operated in an ON/OFF mode or Pulse Width Modulation mode instead of linear mode. This type of driver is very efficient and less complex than a class AB driver. Because of the digital (ON/OFF) nature of the driver, the input signal is digital in nature (pulse width modulation, pulse frequency modulation, etc) and the driver output is also digital in nature. When used to drive an ultrasonic handpiece on or about its resonant frequency, it is desirable to remove all but the fundamental frequency from the driver output so as to limit power dissipation in the handpiece at undesirable frequencies and to eliminate distortion in handpiece voltage and current feedback signals that are used to control handpiece operation. Consequently, a filter circuit is generally inserted between the driver output and the handpiece to remove unwanted harmonics and provide a sine wave drive signal to the handpiece.

Since the driver output is generally a step-up transformer to generate the high voltages required to drive the handpiece and because of filter power dissipation, the filter circuit is generally made of passive components (L, R, C). 2-Pole L-C filters are preferred for lower dissipation and fast roll off of gain with frequency but they suffer from gain peaking around the cutoff frequency.

Typical current designs employ a single fixed output filter for a needle operating at multiple frequencies, primarily to minimize costs and complexity. However, use of a single output filter design can result in undesirable third harmonic frequencies to the handpiece when the phacoemulsification handpiece operates at more than one frequency, particularly when switching between frequencies. Variations in gain experienced at different frequencies may limit the ability to deliver sufficient power at each frequency to adequately drive the handpiece needle.

Single output filters are limited to providing only one fixed relatively low cut-off frequency. An output filter designed to provide gain at the fundamental frequency and rejection of third and higher harmonics for a 38 kHz ultrasonic handpiece cannot maintain a comparable or consistent gain and third harmonic rejection for a 26 kHz ultrasonic handpiece using simple passive filtering.

If the low cut-off frequency for the output circuit is set at too high a level for use with a 38 kHz handpiece a relatively significant third harmonic energy will occur in the output signal resulting in a distorted waveform when driving a 26 kHz handpiece. When a waveform distorts in this manner it becomes difficult for system monitoring circuits to measure the correct voltage and current values used to excite the piezoelectric crystal and to control handpiece operation.

When configuring a single output filter circuit to provide a sufficiently low cut-off frequency for removing the third harmonic distortion from the output signal waveform, resulting from operating the circuit at the first lower frequency such as 26 kHz, the circuit's resultant gain at 38 kHz may be too high or too low depending on placement of the cutoff frequency and the Q of the L-C filter.

Based on the foregoing, it would be beneficial to offer a single output filtering mechanism design for operating an ultrasonic probe at multiple frequencies that overcomes the foregoing drawbacks present in previously known designs used in the ocular surgical environment.

SUMMARY OF THE INVENTION

According to one aspect of the present design, there is provided a system for performing an ocular surgical procedure. The system includes a multiple frequency signal source, a configurable tuned output filter connected to the multiple frequency signal source, and a multiple frequency ultrasonic handpiece. The multiple frequency signal source operates at a first frequency and is configured to drive the configurable filter and the multiple frequency ultrasonic handpiece at the first frequency. The multiple frequency signal source operates at a second frequency and is configured to drive the configurable filter and the multiple frequency ultrasonic handpiece at the second frequency, and the design addresses third harmonic frequency issues for the multiple frequency ultrasonic handpiece. Switchable passive components, such as inductors, resistors, and/or capacitors may be employed in the configurable tuned output circuit, or alternately multiple similar circuits may be employed. As an alternative, a multi-tap transformer may be provided in an appropriate arrangement.

According to another aspect of the present design, there is provided a method of driving a phacoemulsification handpiece configured to operate at multiple frequencies. The method comprises filtering a signal source configured to power the handpiece at more than one frequency using a tuned output filter employing a passive component when the signal source operates at a first frequency. The system further comprises filtering the signal source using the tuned output filter by switching to operation without the passive component when the signal source operates at a second frequency. Switching between operating frequencies provides an output frequency for operating the signal source that substantially matches the tuned output filter.

According to a further aspect of the present design, there is provided a system for operating a phacoemulsification handpiece at multiple operating frequencies. The system comprises a first sine wave signal source configured to deliver a first sinusoidal signal at a first frequency, a second sine wave signal source configured to deliver a second sinusoidal signal at a second frequency differing from the first frequency, and a multi-tap transformer configured to receive the first sinusoidal signal at a first input tap and the second sinusoidal signal at a second input tap. An output tap of the multi-tap transformer connects to the phacoemulsification handpiece and drives the phacoemulsification handpiece at a desired frequency comprising one of the first frequency and the second frequency.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings in which.

DETAILED DESCRIPTION OF THE INVENTION

The following description and the drawings illustrate specific embodiments sufficient to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design is directed to operating an ultrasonic handpiece during an ocular procedure that involves longitudinal and/or transverse motion. The present arrangement may include an electric source configured to provide power to drive the handpiece when connected to a configurable filter for purposes of operating the handpiece at different selected frequencies. For example, the phacoemulsification system may provide for longitudinal needle movements at 38 kHz and may select 26 kHz operation for transverse needle motion. During longitudinal operation, the system configures the output filter for 38 kHz operation. During transverse operation, the system configures the output filter for 26 kHz operation. In order to configure the filter, the present design inserts or removes a passive electrical component using a switch controlled by a device such as an instrument host system.

In general, as used herein, the term "inductor" indicates a passive electrical component configured to block high-frequency signals and conduct low-frequency signals. The term "capacitor" indicates a passive electrical component configured to block low-frequency signals and conduct high-frequency signals.

A low-pass filter design provides for less attenuation at low frequencies and higher attenuation at high frequencies. Band pass filters typically combine inductance with capacitance to pass in-band frequencies while rejecting all frequencies falling out-of-band.

System Example

While the present design may be used in various environments and applications, it will be discussed herein with a particular emphasis on an environment where a surgeon or health care practitioner performs. For example, one embodiment of the present design is in or with an ocular surgical system that comprises an independent graphical user interface (GUI) host module, an instrument host module, a GUI device, and a controller module, such as a foot switch, to control the surgical system.

Figure 1A:
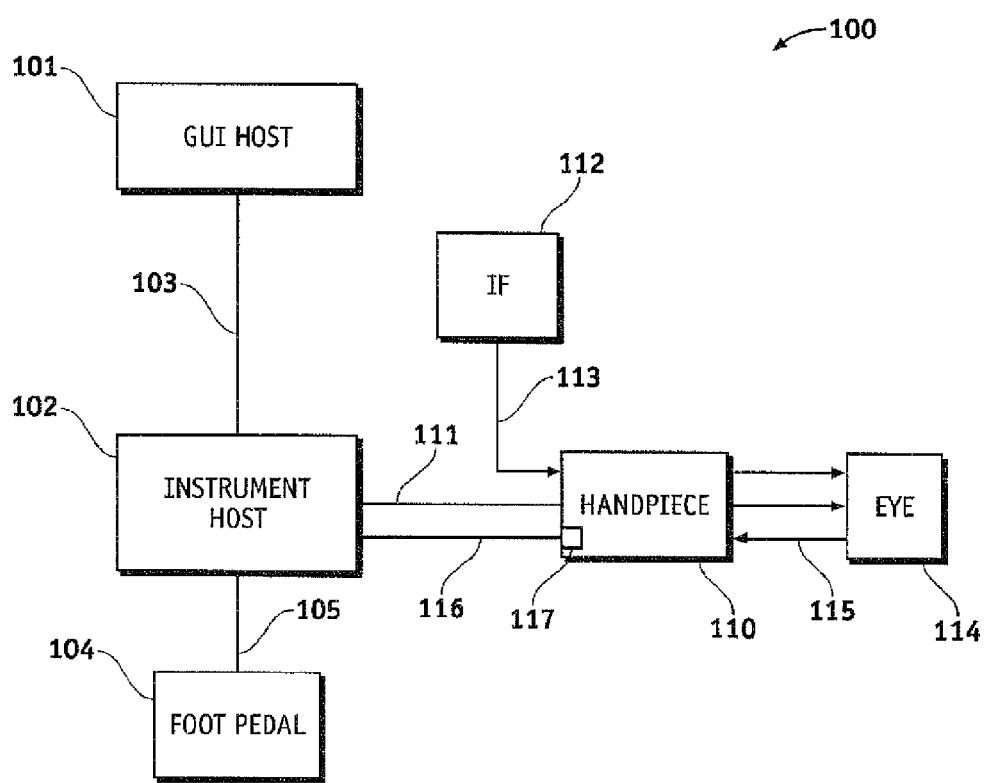
FIG. 1A illustrates an exemplary phacoemulsification/vitrectomy irrigation/aspiration system in a functional block diagram to show the components and interfaces for a safety critical medical instrument system that may be employed in accordance with an aspect of the present invention.

FIG. 1A illustrates an exemplary phacoemulsification/vitrectomy system 100 in a functional block diagram to show the components and interfaces for a safety critical medical instrument system that may be employed in accordance with an aspect of the present invention. A serial communication cable 103 connects GUI host 101 and instrument host 102. GUI host 101 and instrument host 102, as well as any other component of system 100, may be connected wirelessly. Instrument host 102 may be considered a computational device in the arrangement shown, but other arrangements are possible.

A switch module associated with foot pedal 104 may transmit control signals relating internal physical and virtual switch position information as input to the instrument host 102 over serial communications cable 105 (although foot pedal 104 may be wirelessly connected). Instrument host 102 may provide a database file system for storing configuration parameter values, programs, and other data saved in a storage device (not shown). In addition, the database file system may be realized on the GUI host 101 or any other subsystem (not shown) that could accommodate such a file system.

The phacoemulsification/vitrectomy system 100 has a handpiece 110 that includes a needle and electrical means, typically a piezoelectric crystal, for ultrasonically vibrating the needle. The instrument host 102 supplies power on line 111 to a phacoemulsification/vitrectomy handpiece 110. An irrigation fluid source 112 can be fluidly coupled to handpiece 110 through line 113. The irrigation fluid and ultrasonic power are applied by handpiece 110 to an eye, or affected area or region, indicated diagrammatically by block 114. Alternatively, the irrigation source may be routed to eye 114 through a separate pathway independent of the handpiece. Aspiration is provided to eye 114 by one or more pumps (not shown), such as a peristaltic pump, via the instrument host 102, through lines 115 and 116. A surgeon/operator may select an amplitude envelope applied to each pulse via the foot pedal, the instrument host, GUI host, and/or voice command.

In combination with phacoemulsification system 100, the present system enables multiple frequency functionality in or with the phacoemulsification system and may comprise components including, but not limited to, a handpiece (H/P) driver, a tuned circuit containing components such as a capacitor, resistor, inductor, and a switch, such as a MOSFET or a device having similar functionality. The multiple frequency functionality in the present design operates the ultrasonic needle in different cutting modes, where the cutting mode represents the movements or actions of the needle operating within the handpiece.

Figure 1B:
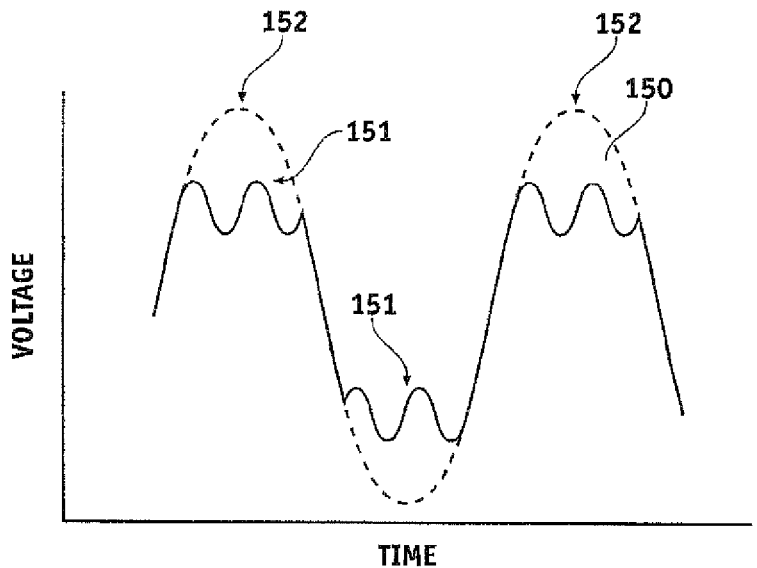
FIG. 1B is an output plot of performance for a dual frequency handpiece design illustrating third harmonic issues.

FIG. 1B illustrates the issues with operating a handpiece at two separate frequencies, illustrating waveform 150 generally exhibiting third harmonic frequency components, which may appear as discontinuities or other signal irregularities similar to responses 151. Response 152 is the filtered waveform. A handpiece voltage or current waveform such as that shown in FIG. 1B is generally unacceptable since it makes control of the handpiece power and cutting efficiency difficult.

Figure 1C:
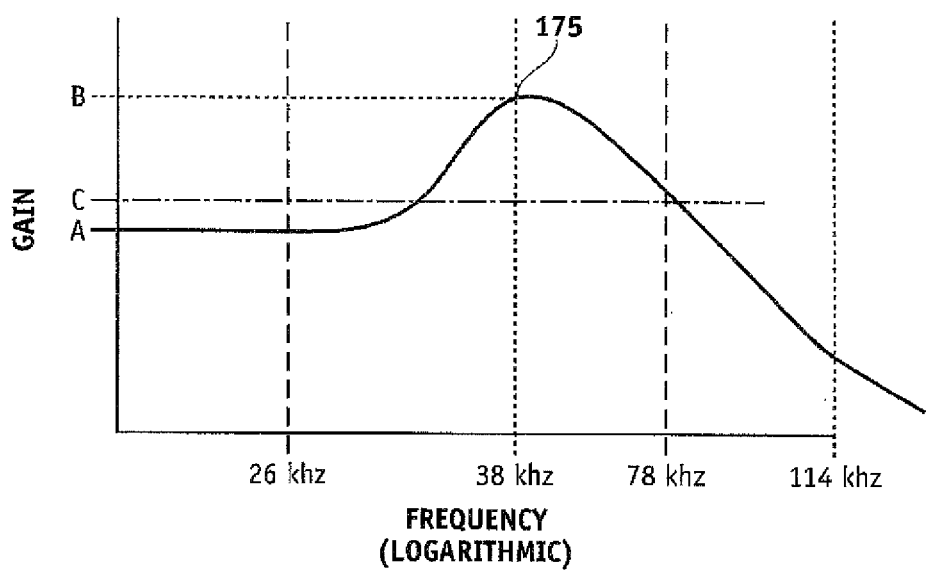
FIG. 1C illustrates a gain-frequency plot for dual frequency handpiece operation showing the issue with third harmonic frequency components using a simple passive L-C filter circuit.

FIG. 1C illustrates a representative frequency versus gain plot for hardware such as has been disclosed and illustrates the issues addressed by the present design. Gain/frequency plot 175 shows 26 kHz and 38 kHz operating frequencies and a resultant value at the third harmonic frequency of the 26 kHz frequency, 78 kHz. Line A illustrates the gain at 26 kHz, line B the gain at 38 kHz, and line C the gain at 78 kHz. The goal of the present design is to minimize or eliminate the gain associated with the third harmonic, or get line C to be as low as possible in the FIG. 1C depiction.

Previous phaco handpiece designs have employed an identification (ID) resistor that indicates handpiece operational parameters. The ID resistor allows the instrument host to configure the handpiece driver for a variety of different handpieces. For example, a first ID resistor may be used to indicate an ultrasonic handpiece configured for 38 kilohertz (kHz) operation, employed for longitudinal cutting action. A second ID resistor has been used to indicate an ultrasonic handpiece configured for 26 kHz operation, where needle movements provide either transverse motion or a mix of longitudinal with transversal motion to realize an elliptical pattern cutting action. A third ID resistor has been used to employ ultrasonic handpieces configured for both 26 kHz and 38 kHz operation, where the surgeon selected the desired operational mode using software executing within the phacoemulsification instrument system.

This manner of marking or indicating the operating frequency of each handpiece using ID resistors permits a surgeon to readily select the handpiece configured for the desired operation, i.e. operation at 38 kHz and/or 26 kHz. In this manner, the surgeon could readily employ desired needle movement and associated cutting action while performing an ocular surgical procedure.

In order to affect a different cutting action in needles previously available, the surgeon selected a software program appropriately configured for operating a particular handpiece. Selecting the appropriately configured software typically involved switching from the electric circuit tuned for the surgeon's prior handpiece, such as a handpiece operating at 38 kHz, to a separate electric circuit tuned for the newly desired 26/38 kHz handpiece, and vice versa.

Typical phacoemulsification handpieces employ a piezoelectric crystal, configured to control the ultrasonic probe cutting needle movement at the desired frequency. Existing designs may employ a tuned electric circuit to realize an output filter configured to drive the piezoelectric crystal at a specific frequency. The tuned electric circuit, typically employing a low pass or band pass filtering scheme, is configured to operate effectively at one single frequency. In the arrangement where the tuned circuit is configured to operate at 38 kHz and the output is driving 26 KHz, the filter can produce a third harmonic frequency energy component, present at 78 kHz. As noted, presence of this third harmonic, in any filtering or needle configuration, is undesirable.

FIGS. 2 through 6 illustrate various embodiments of exemplary multiple frequency phacoemulsification drivers (MFPD) including components and interfaces that may be employed in accordance with various aspects of the present design.

Figure 2:
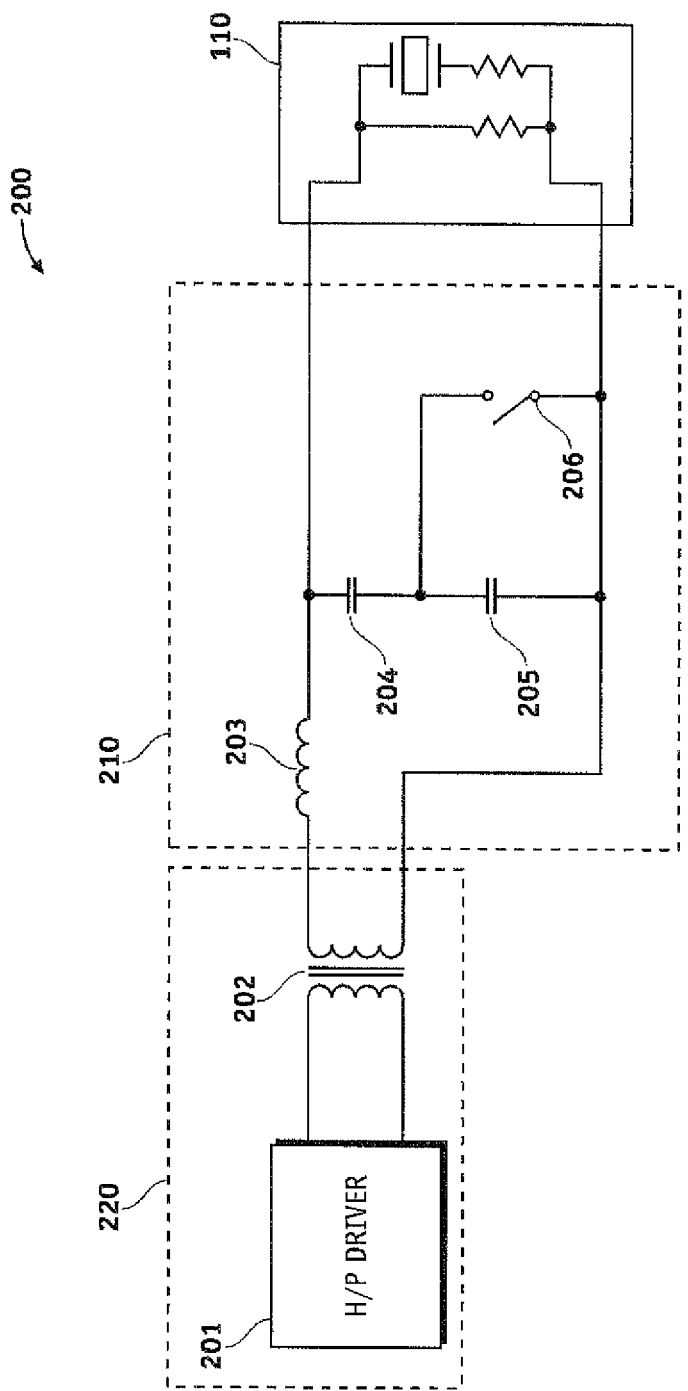
FIG. 2 is a functional block diagram illustrating the multiple frequency phacoemulsification driver ("MFPD") system configured for switching a capacitive component in series with the tuned filter output for modifying the tuned circuit response for the frequency being driven that may be employed in accordance with an aspect of the present design.

FIG. 2 is a functional block diagram illustrating one embodiment of an MFPD system configured for switching a capacitive component in series with the tuned filter for modifying the tuned circuit response for the frequency being driven. The present design contemplates two electric circuit topologies, where MFPD system 200 may operate with either topology via a switch.

The present design effectively switches the pathway for a passive electric component, such as a resistor, capacitor, inductor, and any combinations thereof, where one pathway removes the passive electric component from operating with tuned circuit 210, and the other pathway inserts the passive component for operation with the tuned circuit. Inserting and removing a passive component from tuned circuit 210 may modify the circuit's filtering characteristics, where the tuned circuit 210 uses output of the filter to power handpiece 110. Modification of the circuit's filtering characteristics may include but is not limited to moving the center frequency, bandwidth, quality factor ("Q"), and/or any combinations thereof in order to provide the filter characteristics required to power the handpiece at each desired frequency of operation.

From FIG. 2, multiple frequency phacoemulsification driver 200 thus may include a multiple frequency handpiece driver 201, transformer 202, inductor 203, capacitor 204, capacitor 205, metal-oxide-semiconductor field-effect transistor (MOSFET) operated switch 206, ultrasonic handpiece 110, and electric pathways illustrated with interconnecting lines and line connection points. The electric pathways may be realized using a conductive material, for example wires or 'copper foil' as applied in typical circuit board fabrication. In this arrangement, multiple frequency handpiece driver 201 and transformer 202 may provide an electric signal source 220 for driving tuned circuit 210.

Signal source 220 may include, but is not limited to, a switch mode or class D amplifier configured to operate at multiple frequencies. The amplifier is operated with a duty cycle proportional to the power delivered by switching between, for example, plus and minus 24 volts at the desired frequency. Ultrasonic handpiece 110 in combination with tuned circuit 210 forms a tuned low pass filter and when driven by a mode switching amplifier may provide a sine wave to ultrasonic handpiece 110.

MFPD system 200 is illustrated in FIG. 2 to simply show components that may be used within the present design. The size and shape of the components illustrated are not to scale nor accurately sized, and note that certain components, notably ultrasonic handpiece 110, may interface with tuned circuit 210 but in actuality system 200 provides for powering the attached handpiece device. Further, more or fewer components may be included in the system than are shown in FIG. 2 depending on the circumstances and implementation of the tuned filter configuration.

Referring to FIG. 2, multiple frequency handpiece driver 201 is electrically connected to the primary or input side of transformer 202. The secondary or output side of transformer 202 is connected to inductor 203, configured in series within tuned filter 210 as illustrated. The present design may configure capacitor 204 in series with capacitor 205 and may arrange the two series capacitor in parallel with the output side of transformer 202. Further, the two capacitors are concurrently configured in parallel with ultrasonic handpiece 110.

The present design may arrange MOSFET switch 206 in parallel with capacitor 205. When MOSFET switch 206 is placed in the open position, as illustrated in FIG. 2, capacitor 205 operates in conjunction with the tuned circuit components. When MOSFET switch 206 is placed in the closed position (not shown), capacitor 205 is removed from operation with tuned circuit 210. In this arrangement, MOSFET switch 206 may remove capacitor 205 when closed for operating tuned circuit at one frequency using capacitor 204, and may insert capacitor 205 when open for operating tuned circuit at a different frequency using capacitor 204 with capacitor 205. The present design system and method may change the amount of capacitance in use by tuned circuit 210 and thus change the tuned low-pass filter output signal characteristics.

In this configuration, the instrument host system may operate MOSFET switch 206 based on the desired needle cutting actions selected by the surgeon. A surgeon/operator may select the desired cutting motion using the handpiece, via the instrument host and GUI host, using the foot pedal, and/or voice commands. MOSFET switch 206 may receive signals from instrument host 102 resulting from the surgeon's input to GUI host 101 regarding the desired mode of operation and/or frequency.

Multiple tuned filter options are available in the design of FIG. 2. For example, in one embodiment a component may be arranged such that when operated or switched, the component is either inserted or removed from the circuit and another component removed or inserted. Additionally, one or more electrical sources, operating at two different frequencies, may be used to drive two different tuned circuits, wherein the present design may combine the output from the two filtering circuits and provide power to ultrasonic handpiece 110.

Thus while a single signal source 220 is illustrated in FIG. 2, it is to be understood that this illustration represents an electric source tuned circuit arrangement configured to perform the functionality described herein, and is not limited to a single electric source or a single tuned filter.

The present design's multiple frequency handpiece driver 201, for example a class D switching amplifier or other suitable component, may receive a signal from instrument host 102 to provide power at the selected frequency to ultrasonic handpiece 110, controlled by the surgeon during the procedure such as by a switch or a device such as footpedal 104.

Examples provided herein illustrate a tuned low pass filter. However, the tuned filter may include any filter design suitable for operating the disclosed method, such as a band-pass filter. Further, system 200 is disclosed using inductor 203, MFPD system 200 may use a resistor in place of inductor 203 to realize the tuned circuit. Although the present design is disclosed using one switchable component, the system may include more than one switchable component, in series or in parallel, to modify the output filter cut-off frequency.

The present design is also not limited to switching a capacitive component in and out of a tuned circuit configured in a series arrangement as illustrated in FIG. 2. Other arrangements are possible for modifying tuned circuit 210. FIGS. 3 through 6 provide different tuned circuit examples for use in accordance with the present invention.

Figure 3:
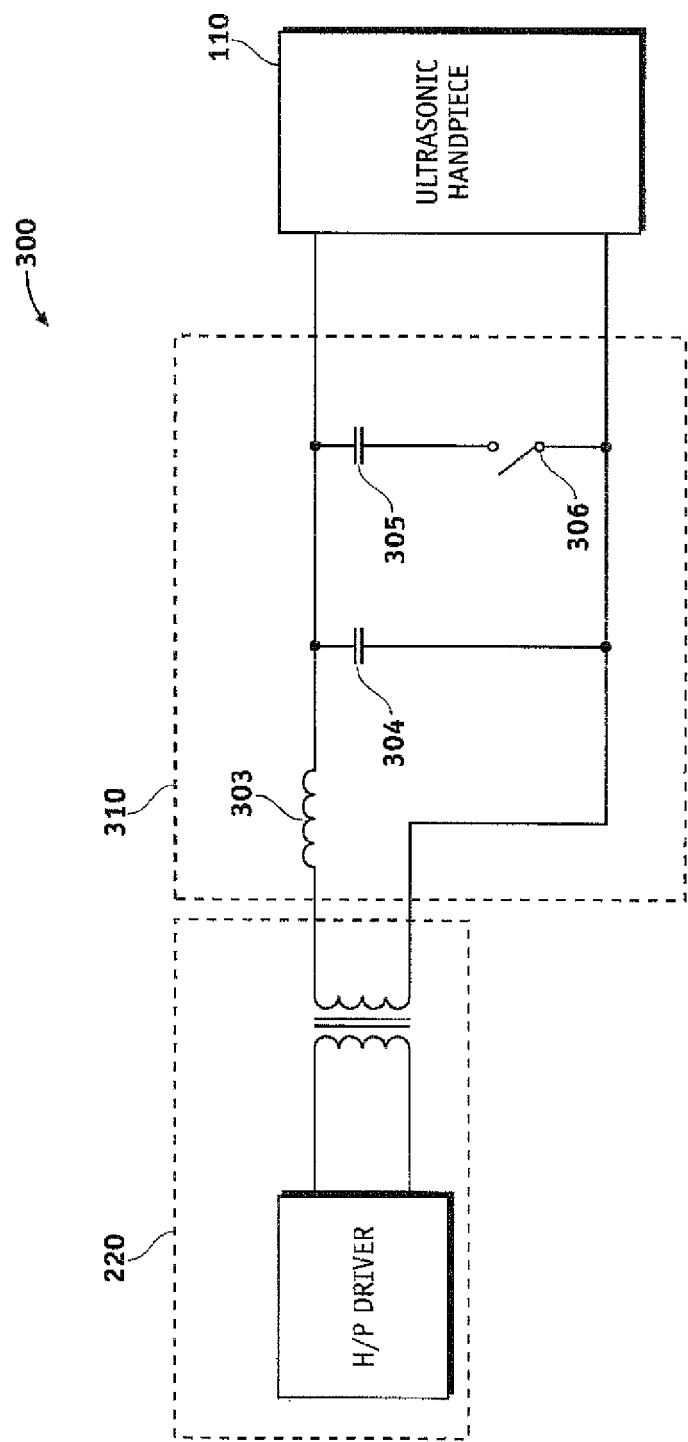
FIG. 3 is a functional block diagram illustrating the MFPD system configured for switching a capacitive component in parallel with the tuned filter output for modifying the tuned circuit frequency response that may be employed in accordance with an aspect of the present design.

FIG. 3 is a functional block diagram illustrating an embodiment of a MFPD system configured to switch a capacitive component in parallel with the tuned filter, modifying the tuned circuit response for the frequency being driven, that may be employed in accordance with an aspect of the present design. It is to be specifically noted that while capacitors and inductors are shown in particular configurations in FIGS. 3-6, components in these embodiments and other embodiments of the design may include multiple components including capacitors, inductors, and resistors, arranged in parallel or in series, to effectuate the functionality described herein. Thus the designs presented are not limited to the components shown but may include other components while still within the scope of the present invention.

From FIG. 3, MFPD system 300 may include signal source 220 configured to drive tuned circuit 310. In this arrangement, the output side of signal source 220 may connect to tuned circuit 310 where inductor 303 is configured in series with capacitor 304 and capacitor 305. Further, the two capacitors are concurrently configured in parallel with ultrasonic handpiece 110, shown in FIGS. 3-6 as a single element but having components as in FIG. 2.

The present design may arrange MOSFET switch 306 in series with capacitor 305. When MOSFET switch 306 is placed in the open position as illustrated in FIG. 3, capacitor 305 is not available for use with tuned circuit 310. In this configuration, MOSFET switch 306 may remove capacitor 305 when placed in the opened position, as illustrated in FIG. 3, where the circuit realized with inductor 303 and capacitor 304 form a tuned filter for operation at a predetermined frequency. The predetermined frequency may be established by selecting filter component values that correspond to the desired frequency for operation. The calculation of component values for desired tuned filter characteristics are known to those skilled in the art.

Closing MOSFET switch 306 may modify tuned circuit 310 by inserting capacitor 305 in parallel with capacitor 304 for operating at a different frequency. In this manner, the present design system and method may change the amount of total capacitance in use by tuned circuit 310 and thus change the tuned low-pass filter output signal characteristics and may avoid third order harmonics issues. Although system 300 is disclosed using inductor 303, MFPD system 300 may use a resistor in place of inductor 303 to realize the tuned circuit.

Figure 4:
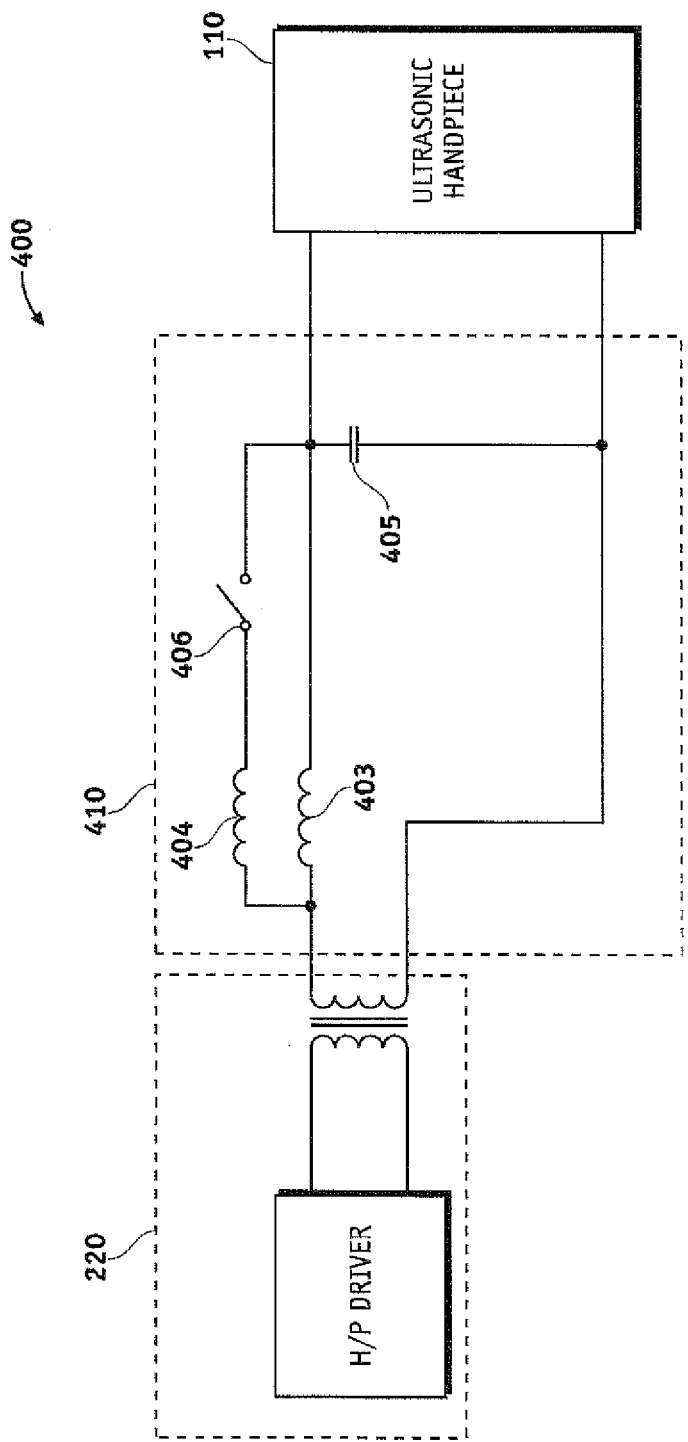
FIG. 4 is a functional block diagram illustrating the present design configured for switching an inductive component in parallel with the tuned filter output for modifying the tuned circuit frequency response that may be employed in accordance with an aspect of the present design.

FIG. 4 is a further diagram illustrating an embodiment configured for switching an inductive component in parallel with the tuned filter output for modifying the tuned circuit frequency response that may be employed in accordance with an aspect of the present design.

MFPD system 400 may include signal source 220 configured to drive tuned circuit 410. In this arrangement, the output side of signal source 220 may connect to tuned circuit 410 where inductor 403 is configured in series with capacitor 405. Further, capacitor 405 is configured in parallel with ultrasonic handpiece 110. The design of FIG. 4 provides MOSFET switch 406 in series with inductor 404. When MOSFET switch 406 is placed in the open position, as illustrated in FIG. 4, inductor 404 is not available for use with tuned circuit 410. In this configuration, MOSFET switch 406 may remove inductor 404 when placed in the opened position, as illustrated in FIG. 4, where the circuit realized with inductor 403 and capacitor 405 form a tuned filter for operation at a predetermined or desired frequency. Closing MOSFET switch 406 may modify tuned circuit 410 by inserting inductor 404 in parallel with inductor 403 in order to operate at a different frequency. In this manner, the present design system and method may change the amount of total inductance in use by tuned circuit 410 and thus change the tuned low-pass filter output signal characteristics. Although system 400 is disclosed using inductors 403 and 404, MFPD system 400 may use a resistor to replace of each inductor to realize the tuned circuit.

Figure 5:
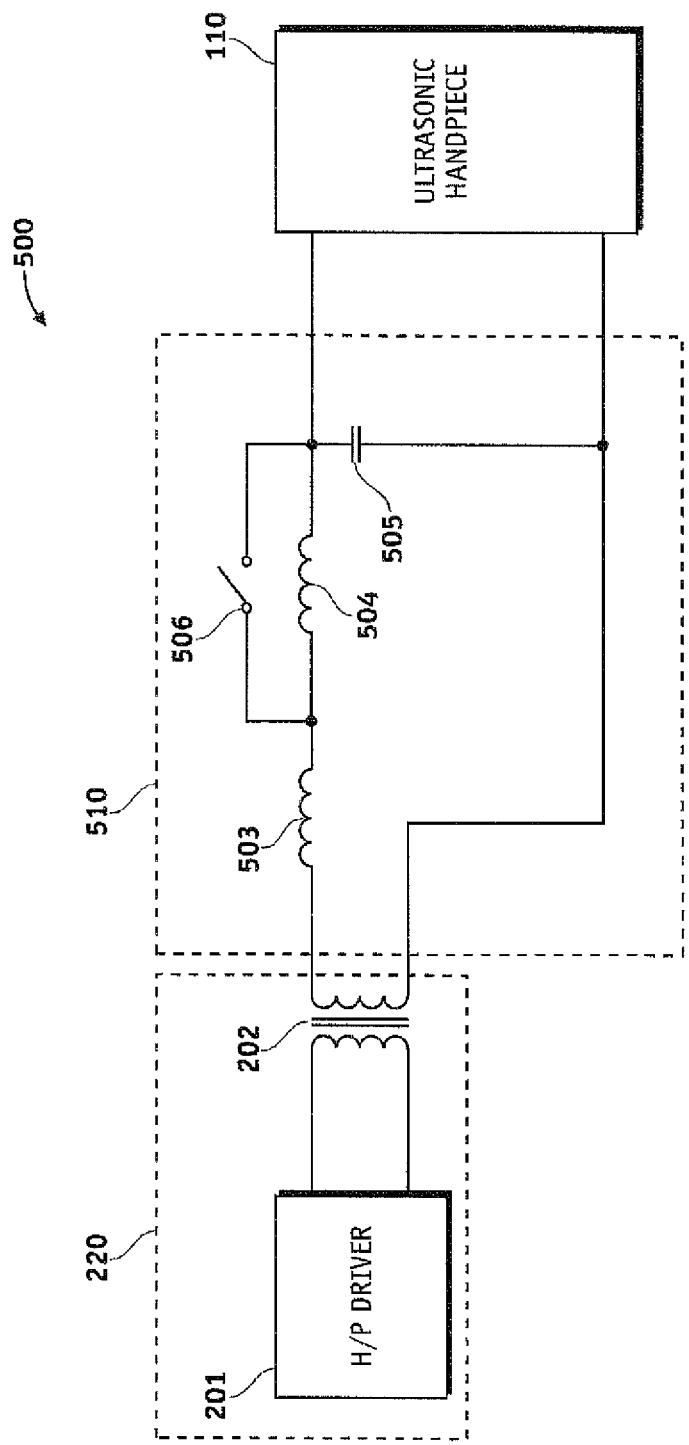
FIG. 5 is a functional block diagram illustrating the present design configured for switching an inductive component in series with the tuned filter output for modifying the tuned circuit frequency response that may be employed in accordance with an aspect of the present design.

FIG. 5 is a functional block diagram illustrating an embodiment of the present design configured for switching an inductive component in series with the tuned filter output for modifying the tuned circuit frequency response in accordance with an aspect of the present design.

MFPD system 500 may include signal source 220 configured for driving tuned circuit 510. In this arrangement, the output side of signal source 220 may connect to tuned circuit 510 where inductor 503 is configured in series with capacitor 505. Further, capacitor 505 is configured in parallel with ultrasonic handpiece 110, and the FIG. 5 design presents MOSFET switch 506 in parallel with inductor 504. When MOSFET switch 506 is placed in the open position, as illustrated in FIG. 5, inductor 504 operates in conjunction with the tuned circuit components. When MOSFET switch 506 is place in the closed position, not shown, inductor 504 is not available for use with tuned circuit 510. In this configuration, switch 506 may remove inductor 504 when placed in the closed position, not shown, where the circuit realized with inductor 503 and capacitor 505 form a tuned filter for operation at a predetermined first frequency. Opening MOSFET switch 506 may modify tuned circuit 510 by removing inductor 504 for operating at a different second frequency. In this manner, the present design system and method may change the amount of total inductance in use by tuned circuit 510 and thus change the tuned low-pass filter output signal characteristics. Although system 500 is disclosed using inductors 503 and 504, MFPD system 500 may use a resistor to replace of each inductor to realize the tuned circuit.

Figure 6:
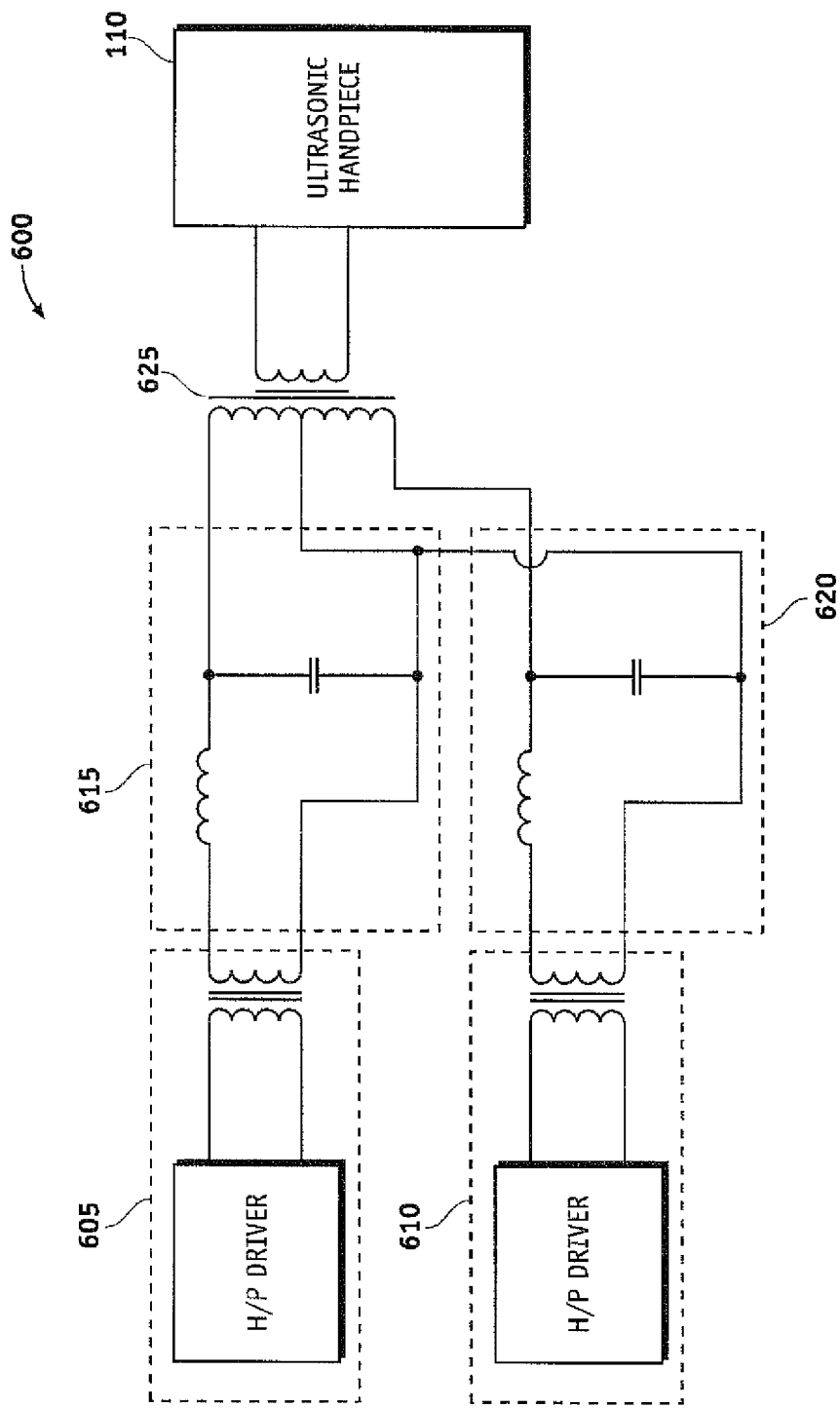
FIG. 6 is a functional block diagram illustrating the present design configured for operating at two different frequencies, where two separate signal sources may be used to drive two different tuned circuits, wherein the present design may combine the output from the two filtering circuits for providing power to the handpiece.

FIG. 6 is a block diagram illustrating operation at two different frequencies, where two separate signal sources drive two different tuned filter circuits. The present design may combine the output from the two filtering circuits and provide power to ultrasonic handpiece 110.

From FIG. 6, MFPD system 600 may include signal source 605 configured for driving tuned filter 615 at a first frequency. In this arrangement, the output side of signal source 605 may connect to tuned filter 615. Further, the output side of tuned filter 615 may connect to a primary input, or tap, of transformer 625. The output of transformer 625 may connect with ultrasonic handpiece 110 in parallel. In this arrangement, signal source 605 operating with tuned circuit 615 may drive ultrasonic handpiece 110 at a first frequency.

MFPD system 600 may include a second signal source 610 configured to drive tuned filter 620 at a second frequency. In this arrangement, the output side of signal source 610 may connect to tuned filter 620. Further, the output side of tuned filter 620 may connect to a second primary input, or tap, of transformer 625. In this arrangement, signal source 610 operating with tuned circuit 620 may drive ultrasonic handpiece 110 at a second frequency.

In this manner, the present design system and method may power ultrasonic handpiece 110 at a first, second, and a combination of these frequencies, such as the aforementioned 26 kHz and 38 kHz, with minimized risk of third harmonic frequency effects. When operating in the combined frequency arrangement, as illustrated in FIG. 6, the present design may power ultrasonic handpiece 110 in both longitudinal and transversal cutting motions simultaneously at the same or differing power levels or frequencies.

In a further embodiment, the system may utilize two transformers in place of transformer 625, where each transformer provides an ultrasonic handpiece driving signal. In this configuration, the handpiece may use two input pins to drive the handpiece, where the output of each transformer is connected to one of the two input pins. Other arrangements may utilize only one input pin of the handpiece with two individual cables connected, where one cable comes from the first transformer and other from the second transformer. Further embodiments may include but are not limited to using a multiple frequency handpiece driver or drivers in combination with adjustable tuned filters such as those illustrated.

Figure 7:
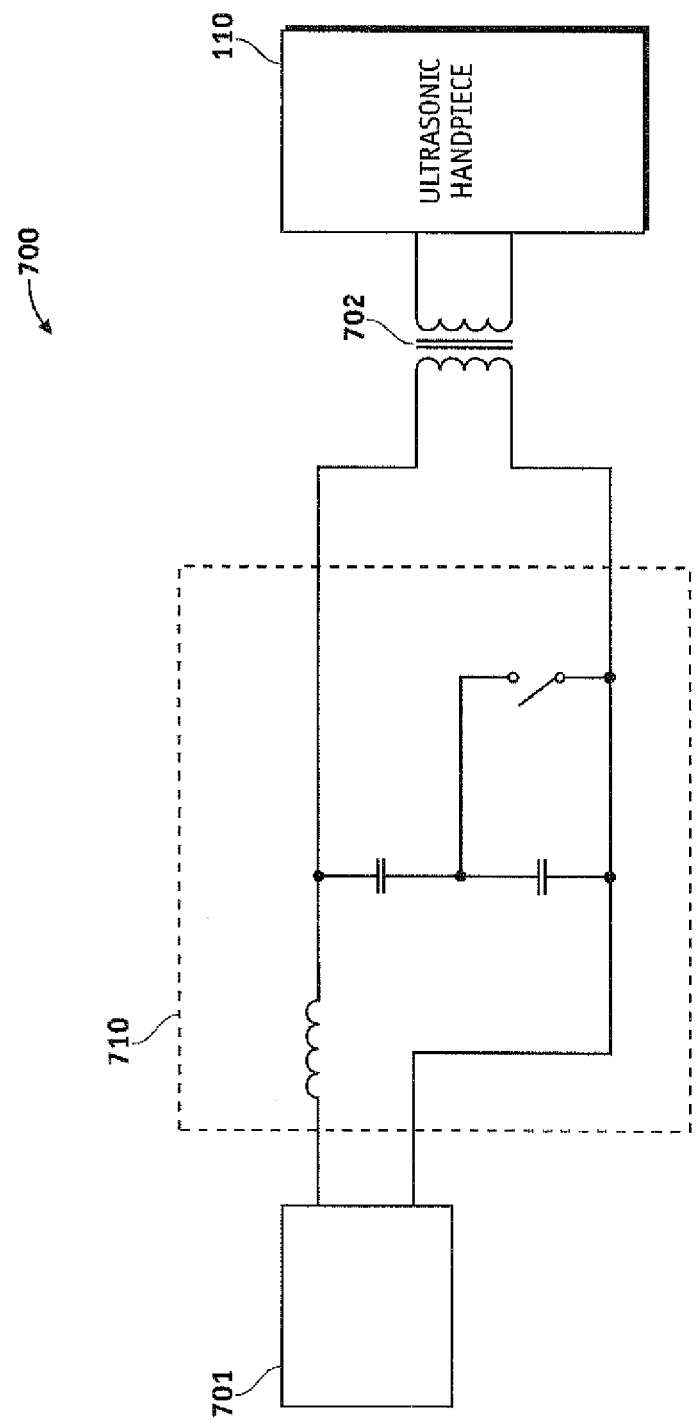
FIG. 7 is a functional block diagram illustrating the present design configured for operating at two different frequencies, where the tuned output filter circuit is positioned between the H/P driver and the primary side of the transformer.

FIG. 7 illustrates operation at two different frequencies, where the tuned output filter circuit is positioned between the handpiece driver and the primary side of the transformer for operation on low level signals. From FIG. 7, MFPD system 700 may include handpiece driver 701 configured as the signal source for driving tuned filter 710. The output side of tuned filter 710 may connect to the primary input, or tap, of transformer 702. In this arrangement, the secondary side of transformer 702 may connect to handpiece 110. The topology for the configurable tuned output filter 710 circuit may be realized using any of the previously disclosed filter embodiments.

Figure 8:
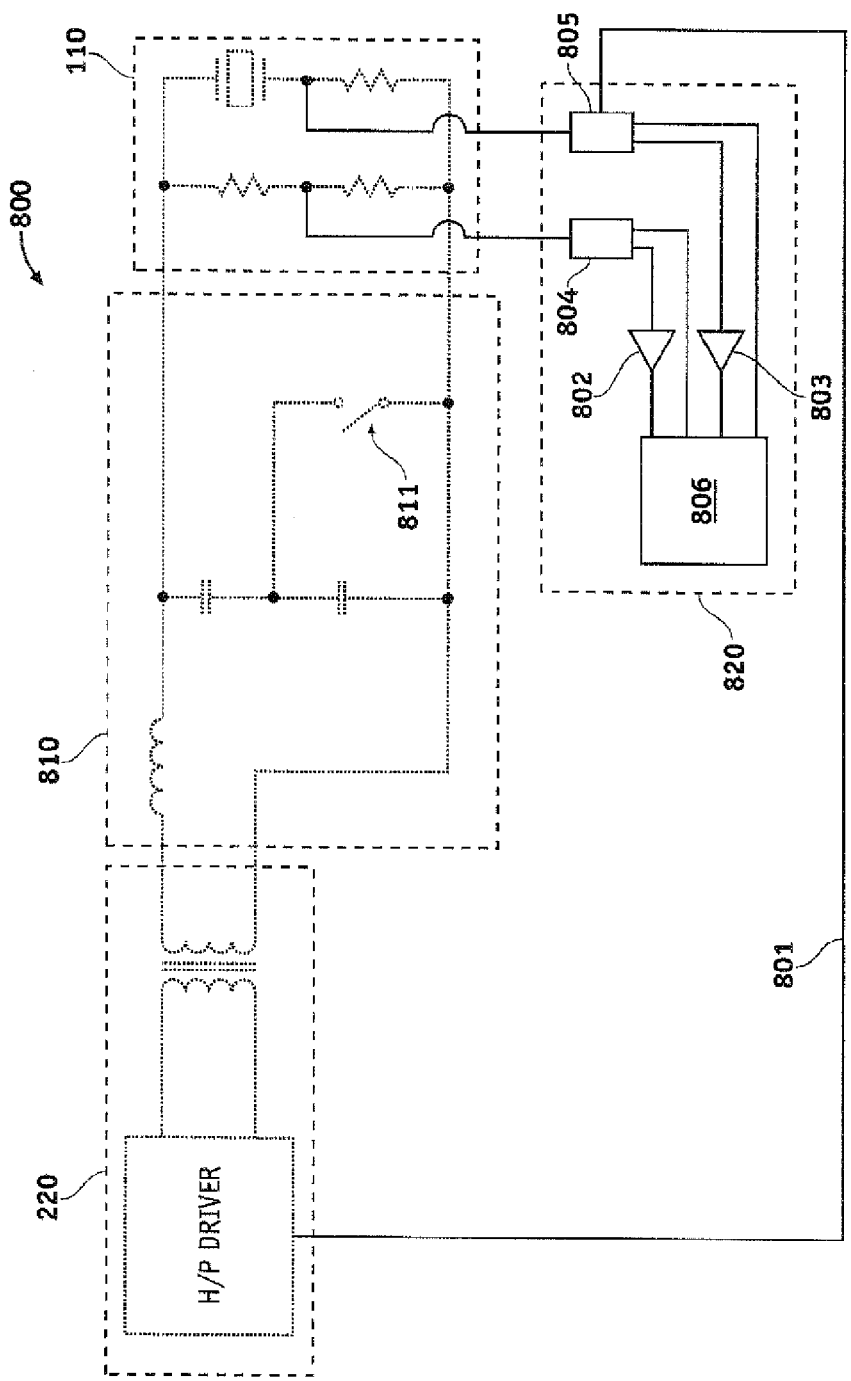
FIG. 8 is a functional block diagram illustrating voltage and current detecting circuit suitable for monitoring and controlling the signal output at the handpiece.

FIG. 8 is a functional block diagram illustrating a monitoring circuit suitable for detecting handpiece voltage and current. Feedback of handpiece driver detected voltage and current enables control of the desired power level to drive the handpiece 110. The present design may detect the phase relationship between voltage and current at the output, i.e. the input to the handpiece for precisely controlling the frequency of operation and maintaining acceptable gain at each operating frequency while ensuring the third harmonic contribution is minimized.

From FIG. 8, MFPD system 800 may measure the operating frequency using monitoring circuit 820. Microcontroller 806 may determine whether to switch representative output filter 810 via switch 811 using a control algorithm configured to enable operation at a different frequency. In other words, microcontroller 806 may continuously determine the operating frequency of the system and determine when to switch to a different frequency. The design of FIG. 8 may detect handpiece voltage and current as illustrated. The detected voltage provides a scaled voltage signal to voltage tracking filter 804 that is fed to voltage comparator 802. The monitoring circuit 820 connects tracking filter 805 to the handpiece driver 200 using line 801 as illustrated. Tracking filter 805 may provide a current signal for input to current comparator 803. The output of tracking filter 804, tracking filter 805, and comparators 802 and 803 are then provided to microcontroller 806 for phase detection and power control. Tracking filters 804 and 805, when used for tracking the feedback signals, may further reduce the third harmonic signal in order to effectively and efficiently control power delivery.

Microcontroller 806 may process received signals to determine the phase relationship between the signals as a function of frequency in order to control handpiece parameters during operation. The present design's ability to remove or reject third harmonic components from the output signal may reduce distortion or phase shifting of the waveform and may improve detection of phase relationships. One skilled in the art understands detecting the phase relationship as a function of frequency.

Figure 9:
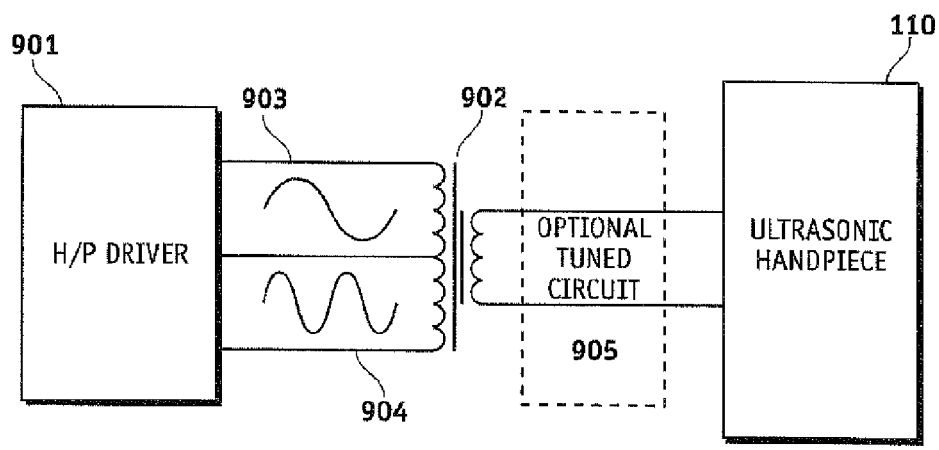
FIG. 9 is a functional block diagram illustrating the present design configured for operating at two different frequencies, where two separate sine-wave signal sources may be used to drive a multi-tap transformer in accordance with an aspect of the current design.

FIG. 9 is a block diagram illustrating the present design configured to again operate two different frequencies, where two separate sine wave signal sources (903, 904) may be used to drive a multi-tap transformer. In this arrangement, a multi-frequency sine wave signal source 901 may provide one or more frequencies, individually and separated in time or in combination at the same time, from sine wave signal sources 903 and 904 where a first signal is provided to transformer 902 first primary input tap and a second signal is provided to transformer 902 second primary input tap. Transformer 902 output tap may connect directly to handpiece 110 as illustrated, but may alternately employ some type of tuned circuitry as shown by optional tuned circuit 905. Use of separate sine wave signals and a multi-tap transformer may eliminate the need for output filtering as previously disclosed, but if desired, the arrangement of FIG. 9 may be used in combination with circuitry and switches disclosed in other embodiments herein as optional tuned circuit 905.

In sum, the present design MFPD system provides for powering and driving the ultrasonic handpiece at two or more frequencies using a configurable filter, such as either a low-pass or band-pass filter, where the instrument host 102 may control the configurable filter using a single software program. The resultant circuitry can minimize negative third harmonic aspects of the dual frequency circuit in certain configurations. A configurable filter where a switchable filter component may be inserted or removed from operation with the filter is provided. Power is applied from a signal source capable of powering output filter and the handpiece at different frequencies of operation.

In one arrangement, the present design's signal source, operating at a first frequency, is configured to drive the output filter where the switchable component is inserted for operation with the filter. In another arrangement, the present design may operate the signal source at a second frequency may drive the output filter where the switchable component is removed from operation. In a further arrangement, the present design may combine the output of two, or more, output filters driven by separate signal sources operating at different frequencies.

Certain additional functionality or components may be provided in the current design. For example, a current and voltage measuring circuit may be configured and connected to the output filter for determining the voltage and phase angle for the signal driving the ultrasonic handpiece.

In short, the present design may involve a specified electric circuit for operation at each frequency range. The MFPD system design may switch electrical components in and out of a circuit for operation at different frequency ranges to configure different output filter responses. The present design system and method may provide for maintaining comparable gain for each supported frequency range while minimizing the third harmonic energy contribution for each frequency range.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A system for performing an ocular surgical procedure, comprising:
  a multiple frequency signal source;
  a configurable tuned output filter connected to the multiple frequency signal source; and
  a multiple frequency ultrasonic handpiece, wherein
  the multiple frequency signal source operates at a first output frequency configured to drive the configurable tuned output filter and the multiple frequency ultrasonic handpiece at the first output frequency;
  the multiple frequency signal source operates at a second output frequency configured to drive the configurable tuned output filter and the multiple frequency ultrasonic handpiece at the second output frequency;
  the configurable tuned output filter is switchable to selectively match the first output frequency and the second output frequency, wherein the configurable tuned output filter substantially passes the first output frequency and substantially attenuates the second output frequency when switched to match the first output frequency, and substantially passes the second output frequency and substantially attenuates the first output frequency when switched to match the second output frequency; and
  the configurable tuned output filter is configured to minimize third harmonic frequency and/or higher harmonic frequency effects for the multiple frequency ultrasonic handpiece.

2. The system of claim 1, wherein the configurable tuned output filter comprises a switchable passive component.

3. The system of claim 2, wherein the switchable passive component decreases frequency effects due to the third harmonic frequency and/or higher harmonic frequency.

4. The system of claim 2, wherein the configurable tuned output filter comprises a capacitor and at least one of an inductor or a resistor, and the switchable passive component further comprises at least one selected from the group consisting of:
  a switched capacitor connected with an additional capacitor;
  a switched inductor connected with an additional inductor; and
  a switched resistor connected with an additional resistor.

5. The system of claim 1, wherein the configurable tuned output filter comprises a plurality of circuits, wherein switching operation switches from a first tuned output circuit tuned to the first output frequency to a second tuned output circuit tuned to the second output frequency.

6. The system of claim 1, further comprising a monitoring circuit configured to monitor parameters of a configurable tuned output circuit.

7. The system of claim 6, further comprising a microcontroller configured to interface with the monitoring circuit and switch between frequencies based on a monitored operating frequency received from the monitoring circuit.

* * * * *